United States Patent [19]

Lyon et al.

[11] Patent Number: 4,906,564

[45] Date of Patent: Mar. 6, 1990

[54] ANTIGENIC DETERMINANTS RECOGNIZED BY ANTIBODIES OBTAINED USING A PATHOGENIC AGENT OR A DERIVATIVE THEREOF THAT PRESENTS A RESTRICTED SET OF ANTIGENS

[75] Inventors: Jeffery A. Lyon, Silver Spring, Md.; Jeffrey L. Chulay, Washington, D.C.; Alan W. Thomas, Silver Spring, Md.; Russell J. Howard, Los Altos Hills, Calif.; James L. Weber, Marshfield, Wis.

[73] Assignee: The United States of America as represented by the Secretary of the Army, Washington, D.C.

[21] Appl. No.: 25,741

[22] Filed: Mar. 13, 1987

[51] Int. Cl.$^4$ .................. G01N 33/561; G01N 33/569
[52] U.S. Cl. .......................................... 435/7; 435/5; 435/29; 530/350; 530/387; 530/412; 530/413
[58] Field of Search ................. 435/5, 7, 29; 530/350, 530/387, 412, 413

[56] References Cited

U.S. PATENT DOCUMENTS 4,722,891  2/1988  Drutz et al. ............................ 435/7

OTHER PUBLICATIONS

Robey et al., "Characterization of Envelope and Core Structural Gene Products of HTLV—III with Sera from AIDS Patients", Science, 228, (05/03/85), 593–595.

Robert—Guroff et al., "In Vitro Generation of an HTLV—III Varient by Neutralizing Antibody", Journal of Immunology, 137, (11/15/86), 3306–3309.

Cochrane et al., "Monoclonal Antibodies Identify the Protective Antigens of Sporozoites of Plasmodium Knowlesi", Proc. Natl. Acad. Sci. USA, 79, (1982), 5651–5655.

Primary Examiner—Christine M. Nucker
Attorney, Agent, or Firm—Werten F. W. Bellamy

[57] ABSTRACT

A method provides peptides that are antigenic determinants identified by antibodies obtained using intact pathogenic agents that present a restricted set of antigens to surveillance by the immune system.

8 Claims, 6 Drawing Sheets

```
                                                               48
GAA TTC ATA TTA GAT AAT TTG AAA ACA AGT GTT TTA AAT AAA TTA AAA
Glu Phe Ile Leu Asp Asn Leu Lys Thr Ser Val Leu Asn Lys Leu Lys

96
GAT TTA TTA TTA AGA TTA TTA TAC AAA GCA TAT GTA TCA TAT AAG AAA
Asp Leu Leu Leu Arg Leu Leu Tyr Lys Ala Tyr Val Ser Tyr Lys Lys

144
AGA AAA GCT CAA GAA AAA GGA TTA CCA GAA CCT ACT GTT ACT AAT GAA
Arg Lys Ala Gln Glu Lys Gly Leu Pro Glu Pro Thr Val Thr Asn Glu

192
GAA TAT GTT GAA GAA TTA AAG AAA GGT ATT CTA GAT ATG GGT ATC AAA
Glu Tyr Val Glu Glu Leu Lys Lys Gly Ile Leu Asp Met Gly Ile Lys

240
TTA TTA TTT AGT AAA GTT AAA AGC CTA TTA AAA AAA TTA AAA AAT AAA
Leu Leu Phe Ser Lys Val Lys Ser Leu Leu Lys Lys Leu Lys Asn Lys

288
ATA TTC CCT AAG AAA AAA GAA GAT AAT CAA GCA GTA GAT ACC AAA AGT
Ile Phe Pro Lys Lys Lys Glu Asp Asn Gln Ala Val Asp Thr Lys Ser

336
ATG GAA GAA CCC AAA GTT AAA GCA CAA CCA GCT CTT AGA GGT GTT GAA
Met Glu Glu Pro Lys Val Lys Ala Gln Pro Ala Leu Arg Gly Val Glu

384
CCA ACG GAA GAT TCT AAT ATT ATG AAC AGT ATT AAT AAT GTT ATG GAT
Pro Thr Glu Asp Ser Asn Ile Met Asn Ser Ile Asn Asn Val Met Asp

432
GAA ATT GAT TTC TTT GAA AAA GAA TTA ATC GAA AAT AAT AAT ACA CCT
Glu Ile Asp Phe Phe Glu Lys Glu Leu Ile Glu Asn Asn Asn Thr Pro

480
AAT GTT GTA CCA CCA ACT CAA TCA AAA AAA AAA AAC AAA AAT GAA ACT
Asn Val Val Pro Pro Thr Gln Ser Lys Lys Lys Asn Lys Asn Glu Thr

528
GTA TCT GGT ATG GAT GAA AAT TTT GAT AAT CAT CCT GAA AAT TAT TTT
Val Ser Gly Met Asp Glu Asn Phe Asp Asn His Pro Glu Asn Tyr Phe

576
AAA GAA GAA TAT TAT TAT GAT GAA AAT GAT GAT ATG GAA GTA AAA GTT
Lys Glu Glu Tyr Tyr Tyr Asp Glu Asn Asp Asp Met Glu Val Lys Val

624
AAA AAA ATA GGT GTC ACA TTA AAA AAA TTT GAA CCA CTT AAA AAT GGA
Lys Lys Ile Gly Val Thr Leu Lys Lys Phe Glu Pro Leu Lys Asn Gly

672
AAT GTT AGT GAA ACC ATT AAA TTG ATT CAT TTA GGA AAT AAA GAT AAA
Asn Val Ser Glu Thr Ile Lys Leu Ile His Leu Gly Asn Lys Asp Lys

720
AAA CAC ATT GAA GCT ATA AAC AAC GAT ATT CAA ATT ATT AAA CAA GAA
Lys His Ile Glu Ala Ile Asn Asn Asp Ile Gln Ile Ile Lys Gln Glu

768
TTA CAA GCT ATT TAT AAT GAA CTT ATG AAT TAT ACA AAT GGA AAC AAA
Leu Gln Ala Ile Tyr Asn Glu Leu Met Asn Tyr Thr Asn Gly Asn Lys

804
AAT ATT CAA CAA ATA TTT CAA CAA AAT ATT CTA GAA
Asn Ile Gln Gln Ile Phe Gln Gln Asn Ile Leu Glu
```

FIG. 7

ANTIGENIC DETERMINANTS RECOGNIZED BY ANTIBODIES OBTAINED USING A PATHOGENIC AGENT OR A DERIVATIVE THEREOF THAT PRESENTS A RESTRICTED SET OF ANTIGENS

BACKGROUND OF THE INVENTION

The present invention relates to a class of peptides that are antigenic determinants identified by antibodies obtained using a virus, bacterial cell or other pathogenic agent, or a derivative of such an agent, that presents a restricted set of antigens to surveillance by the immune system. The present invention also relates to immunogens that comprise such an antigenic determinant, and to vaccines containing such an immunogen.

Development of an effective, practical vaccine against a given pathogenic agent often hinges on identifying and characterizing targets of antibody-mediated immunity against that agent. Typically, the search for such target antigens is complicated by difficulties encountered in selecting, from among a large number of antigens contained in the pathogenic agent, those that are important in eliciting a protective immune response. Even a relatively simple pathogen like a poliovirus, among the least complex of small spherical viruses, may comprise many antigens; yet only a subset of these are positioned, at one time or another during the life cycle of the virus, so as to be accessible to antibody-binding.

The problems of identifying members of this subset, and of characterizing the antigenic determinants they present, is exacerbated in the case of more complicated pathogens, such as trypanosome and malaria parasites, by a larger number of antigens and a more diverse range of life forms. For example, within the human host, the life cycle of the malaria parasite encompasses four different stages (sporozoite, exoerythrocytic, asexual erythrocytic, and gametocytic) and numerous forms, each morphologically and antigenically distinct. There is also antigenic diversity in natural parasite populations, including expression of different isozymes, different sensitivities to antimalarial drugs, and expression of alternative antigenic determinants ("epitopes") on particular malarial proteins. Finally, malaria parasites may express new antigenic phenotypes through mutation or through recombination within a gene.

Existing methods for identifying particular antigens as prime immunological targets derive from one of several approaches to epitope-mapping. By one approach, monoclonal antibodies can be used to compare the relative rate of chemical modification of residues of a protein antigen in the presence or absence of a specific monoclonal antibody, thereby permitting one to deduce the location of the epitope from the differential chemical reactivity of amino acid side chains. See, e.g., Burnens et al, *Science* 235: 780 (1987). Alternatively, a monoclonal antibody can also be used to identify synthetic peptides that are putative epitopes or functional analogs thereof. Ballou et al., *Science* 228: 996 (1985). Additionally, monoclonal escape mutants can be characterized by means of monoclonal antibodies. Hogle et al., *Sci. Amer.* 256: 42 (1987).

These applications, while useful, present the disadvantage that prerequisite functional monoclonal antibodies are rarely available and are not readily prepared for many antigens. Alternatively, synthetic peptides can be used to induce functional monospecific antibodies (Ballou et al., 1985). By exploiting the ability of intact infectious organisms to adsorb out peptide-specific antibody from neutralizing antiserum, synthetic peptides can also be used to identify epitope specificities recognized by functional antibodies in vivo. Both of these approaches typically require the synthesis of a vast number of different peptides, however, and especially when epitopes are formed by amino acids that are noncontiguous in the antigen.

SUMMARY OF THE INVENTION

It is therefore an object of the present invention to provide methodology for identifying antigens, and particularly antigenic determinants, that are made accessible to antibody binding during the life cycle of an infectious organism, which methodology requires neither monoclonal antibody nor synthetic peptide.

It is also an object of the present invention to provide an immunogen that includes an antigenic determinant presented to immune-system surveillance by a parasite, virus or other pathogen.

It is a further object of the present invention to provide malaria antigens that can be used in an antimalaria vaccine.

In accomplishing the foregoing objects, there has been provided, in accordance with one aspect of the present invention, a method for identifying antigenic determinants of a pathogenic agent, comprising the steps of (A) providing a sample comprising a plurality of intact units of a pathogenic agent, (B) contacting the sample with a heterogeneous mixture of antibodies from functional immune serum, such that an antibody from the mixture binds to an antigenic determinant presented by an intact unit of the plurality, (C) isolating the antibody from the sample, and (D) using the antibody to probe a heterogeneous mixture of antigens produced by the pathogenic agent. In a preferred embodiment, step (D) comprises the use of the antibody to probe a series of libraries, each library in the series yielding different expression products.

In accordance with another aspect of the present invention, there has been provided, in substantially pure form, a *P. falciparum* protein selected from the group of p51, p71, p90, p101, p173 (triplet) and p230.

There has also been provided, in accordance with yet another aspect of the present invention, an antimalarial vaccine comprising at least one of the aforesaid *P. falciparum* proteins. In one preferred embodiment, the vaccine further comprises at least one other *P. falciparum* antigen selected from the group of gp195, p113, p83, p73, p67, p45 and gp45.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIG. 1 shows the fluorographic pattern obtained after sodium dodecyl sulfate-polyacrylamide gel electrophoresis (SDS-PAGE) of [$^3$H]-isoleucine-labeled immune clusters of merozoites (ICM) and normal merozoites (NM) and of various fractions of ICM and NM. Specific antigens are identified by molecular weight on the left side of the figure. Arrows on the right side of the figure are molecularweight markers. From top to bottom: (A) myosin, 200,000; (B) phosphorylase B, 92,500; (C) serum albumin, 69,000; (D) ovalbumin, 46,000; (E) carbonic anhydrase, 30,000; and (F) lysozyme, 14,000 (migrated with dye front).

Figure 6:
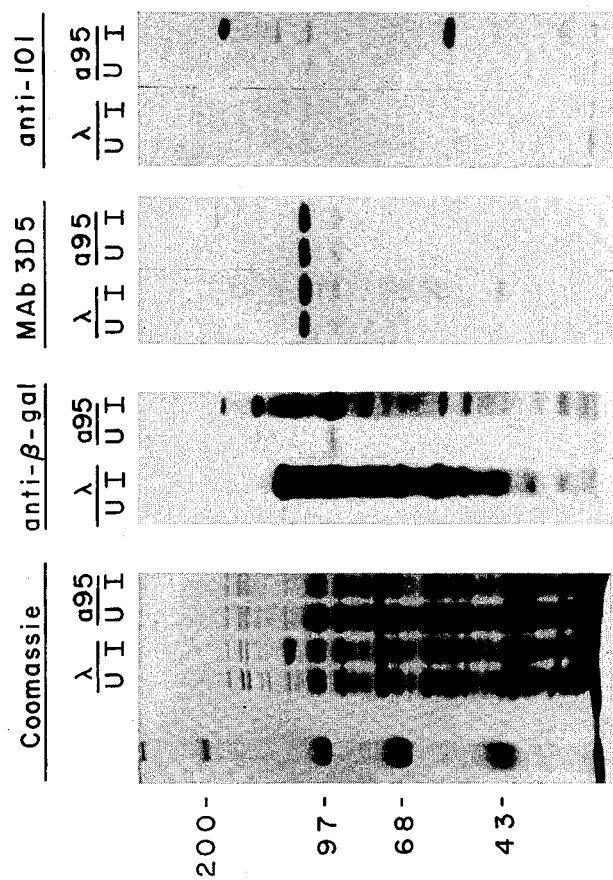

FIG. 6 shows results of an experiment in which expression proteins from *E. coli* Y1089 containing lysogenic phage a95, or control phage (λ), were cultured without IPTG induction (U) or with IPTG induction (I); were separated by SDS-PAGE; and then stained with Coomassie blue (left panel) or electroblotted onto nitrocellulose. In the latter case, immunoblots were probed with antibodies against β-galactosidase (anti-β-gal), probed with a monoclonal antibody that recognized p101 (MAb 3D5), or probed with antibodies from immune serum that were affinity purified and that specifically recognized p101 (anti-101).

FIG. 7 shows the nucleotide sequence and deduced amino acid sequence of the first 804 base pairs of clone a95.

DETAILED DESCRIPTION OF PREFERRED EMBODIMENTS

It has been discovered that antigenic determinants presented to immunological surveillance by a restricted set of the total number of antigens contained in a particular pathogen can be identified, pursuant to the present invention, using intact units of the pathogenic agent as affinity-substrates, in effect, for cognate antibody that is present in functional immune serum. For purposes of the present description, the phrase "functional immune serum" (FIS) is used to denote blood serum from an individual, human or animal, whose immune system has been challenged by a pathogenic agent, or by an immunogenic extract of that pathogen, such that the serum contains functional antibodies against an intact unit (viral particle, bacterial cell, cancer cell, whole parasite) of the pathogen. In the present context, "intact unit" can also refer to an entire molecule when the pathogenic agent is, for example, a snake venom or other toxin or allergen which raises functional antibodies in vivo.

In accordance with the present invention, FIS is brought into contact with intact units of the pathogenic agent of interest, resulting in the formation of immune complexes around the pathogen that are comprised of (i) antigen which is accessible in the intact unit to antibody-binding and (ii) FIS antibody which recognizes an antigenic determinant presented by the antigen. In accordance with one preferred embodiment of the present invention, the immune-complexing is conducted with metabolically labeled antigen—typically labeled with a radionuclide-containing amino acid needed by the pathogenic agent for protein synthesis—in order that antigens within the immune complexes can be identified after electrophoretic separation, as described in greater detail below.

After complexing, unbound antibody is washed away and the immune complexes recovered. The complexes can be obtained, for example, by detergent extraction: the intact units of the pathogen, previously exposed to FIS, are treated with a mild solution of a detergent like Triton X-100 (Biorad) at a pH which is determined empirically to be solubilizing. The immune complexes thus recovered can then be analyzed using gel electrophoresis, e.g., the SDS-PAGE technique described by Laemmli, *Nature* 227: 680 (1970).

Prior to analysis by gel electrophoresis, antigen-antibody complexes can be precipitated by means of staphylococcal protein A. Since only antibodies are precipitated by protein A, its use in the present context provides an indication that the antigens identified fluorographically in a particular precipatated fraction after gel electrophoresis were actually part of an immune complex.

In another preferred embodiment, recovery of immune complexes as described above can be followed by dissociation of the complexes and isolation of the constituent antibody. Dissociation is preferably effected by acidification, followed by centrifugation to separate soluble and insoluble fractions. Thereafter, the soluble fraction is recovered and neutralized. The antibodies obtained in this fashion recognize the epitope presented by the complexed antigen in the intact unit of the pathogenic agent. Accordingly, the antibodies can be employed as indicators for the presence, in a heterogeneous mixture, of an antigen containing the complete epitope.

For example, an electrophoretic gel across which crude (total) or affinity-purified antigen from a pathogen is separated can be blotted and then probed with antibody dissociated from an immune complex, to identify those antigens containing the antigenic determinant recognized by the antibody. In a particularly preferred embodiment, a complexing antibody prepared as described above is used to probe the translation products obtained upon expression of a collection or "library" of fragments produced (typically, via restriction-enzyme digestion) from genetic material of a pathogenic organism, following Young and Davis, *Science* 222: 778 (1983).

In the following illustrations of the present invention, the pathogen of interest is *Plasmodium falciparum*, one of four species of human malaria parasite and the cause of nearly all malaria-related deaths. But the present invention is not limited to *P. falciparum*, or to the class of malarial pathogenic agents. As indicated above, the present invention can be used to produce epitopic peptides in the context of virtually any pathogenic agent for which functional antibody can be made available via conventional in vitro and in vivo techniques, such as infection and recovery, with or without drug cure, or immunization with dead or attenuated pathogenic organisms (or fractions thereof), allergens, toxins and the like, with or without adjuvants, and then collection of immune serum, or production of monoclonal antibodies, in natural or experimental hosts. Thus, the peptides of the present invention include those prepared using FIS antibodies against HIV and other viruses, bacterial pathogens, trypanosome and other parasites, neoplastic cells, and the range of immunogenic toxins and allergens.

Unless otherwise indicated, a protein (p) or glycoprotein (gp) identified in the following examples as a *P. falciparum* antigen is designated by its apparent relative molecular mass ($M_r$). Such indicia of molecular weight may vary slightly from laboratory to laboratory, depending on processing parameters; this variation can be easily accomodated through the use of internal molecular-weight standards.

EXAMPLE 1

Characteristics of Radiolabeled Antigens from *P. falciparum* Immune Complexes During the life cycle of malaria parasites, blood stage merozoites make a transitory extraerythrocytic appearance as they are released from mature schizont-infected erythrocytes and invade new erythrocytes. When *Plasmodium falciparum* parasites are cultured in the presence of some immune monkey or human sera, i.e., sera containing appropriate functional antibodies (as defined below), merozoites do not disperse after rupture of schizont-infected cells but instead are agglutinated by antibodies to form immune clusters of merozoites (ICM), and parasite growth is inhibited, as described, for example, by Chulay et al, *Am. J. Trop. Med. & Hyg.* 30: 12 (1981). Electron micrographs of ICMs show that they possess a thick coat of antigen-antibody complexes. Only a restricted subset of the antigens synthesized by the parasite are found within these complexes.

Preparation of Functional Immune Serum: For use in characterizing members of the restricted set of antigens readily accessible to antibody-binding in ICMs, FIS from Aotus monkey A076 was prepared according to the following schedule:

| Day | Treatment |
| --- | --- |
| 0 | Infected (5 × $10^6$ CAMP IRBC*) |
| 10 | Chloroquine** |
| 25 | Challenge (1 × $10^7$ CAMP IRBC) |
| 206 | Challenge (5 × $10^8$ CAMP IRBC) |
| 714 | Challenge (5 × $10^8$ CAMP IRBC) |
| 777 | Serum Collected |

*CAMP IRBC: red blood cells infected with the "Camp" strain pf *P. falciparum*
**Antimalarial drug (Winthrop Laboratories).

As described by Chulay et al (1981), A076 immune sera caused ICM formation and inhibition of invasion during in vitro culture of Camp strain *P. falciparum*. After it had been immunized by infection and drug cure, monkey A076 was completely protected against repeated in vivo challenges with the homologous parasite in autologous red cells. The growth inhibitory activity was restricted to the IgG fraction of A076 serum. FIS was prepared by pooling three immune A076 sera obtained 47, 61 and 75 days after the third rechallenge with 5×$10^8$ parasites on day 714 after the initial infection. At a 1:10 dilution, these sera gave an average of 53% inhibition of reinvasion of the Camp strain. (Preinfection serum from monkey A076 was used as a negative control.) Sera were stored at −80° C. and were heat inactivated before use.

Metabolic labeling and purification of merozoites: Synchronous cultures of schizont-infected erythrocytes were labeled for 4 hours by using 30 μCi/ml [$^3$H]-isoleucine (Amersham) in isoleucine-deficient medium. At the end of the culture period, the culture volume was reduced 10-fold by aspirating the excess medium, and enzyme inhibitors were added. Merozoites were separated from uninfected, schizont-infected, and ring-infected erythrocytes by centrifuging at 1500×G for 60 g-minutes per millimeter of fluid height (60 g-min/mm) in a centrifuge tube. Centrifugation was at room temperature performed with a swinging bucket rotor. The supernatant (containing merozoites) was collected and centrifuged at 1500×G for 300 g-min/mm. Under these conditions, 85% of the free merozoites were recovered (calculated by counting fluorescent nuclei stained with the use of acridine orange, and comparing the number of merozoites in the 60 g-min/mm supernatant with the number recovered in the 300 g-min/mm pellet). Merozoites were washed three times, alternately resuspending in 0.5 ml of PBS plus enzyme inhibitors and centrifuging at 3,000×G for 3 minutes in an Eppendorf centrifuge. The final merozoite pellet was extracted in pH 8 TX100 (Tris-buffered saline containing 1 mM EDTA and 1% Triton X-100) which contained enzyme inhibitors (30 μl per 1×$10^8$ starting schizont-infected erythrocytes). The soluble fraction was stored at −80° C.

Metabolic labeling and purification of schizont-infected erythrocytes: The first pellet (60 g-min/mm) recovered during the purification of metabolically labeled merozoites contained uninfected red blood cells, red blood cells infected with schizonts and rings, and some merozoites. To purify the schizonts, this pellet was resuspended in 8 ml of complete medium containing enzyme inhibitors and was centrifuged through Metrizamide gradients as described by Pavia et al, *Am. J. Trop. Med. Hyg.* 32: 675 (1983), except that 17% Metrizamide was used instead of 15%. Purified schizont-infected erythrocytes were washed and extracted in pH 8 TX100, and the soluble fraction was frozen at −80° C.

Metabolically-labeled immune clusters of merozoites (ICM) and normal merozoites: Metrizamide-purified schizont-infected erythrocytes were cultured in isoleucine-deficient medium containing 10% immune serum for ICM, or 10% preinfection serum for normal merozoites (NM), and 30 μCi/ml [$^3$H]-isoleucine at a cell density of 1×$10^7$ schizonts/ml. After 4 hours, enzyme inhibitors were added to the cultures and parasites were collected by centrifugation at 1500×G for 300 g-min/mm. Unbound antibodies were removed by washing three times with 0.5 ml of PBS or wash medium containing the enzyme inhibitors. Centrifugations were for 1 min at 13,000×G. Parasites were extracted by using pH 8 TX100 and enzyme inhibitors at a ratio of 40 μl of pH 8 TX100 per 1×$10^7$ initial schizonts. The soluble and insoluble fractions were separated by centrifugation for 3 minutes at 13,000×G. Pellets were washed three times with pH 8 TX100 before processing for SDS-PAGE.

Electrophoresis: Antigen analysis was by discontinuous SDS-PAGE performed with slab gels containing an 8 to 12% linear acrylamide gradient and a 3% acrylamide stacking gel. Molecular-weight standards ($^{14}$C-labeled) were obtained from Amersham. Protein A (Pansorbin) immunoprecipitates and pH 8 TX100 pellets were prepared for electrophoresis by boiling in 50 μl of SDS sample buffer (2% SDS, 10% 2-mercaptoethanol, and 62.5 mM Tris buffer at pH 6.8) for 10 minutes. The pH 8 TX100 soluble antigen fractions were prepared for electrophoresis by diluting two parts with one part of three-times concentrated SDS sample buffer. Fluorography was performed by treating the gels with En³Hance (New England Nuclear) and exposing them to hypersensitized Kodak XAR-2 film at −80° C.

Figures 1, 2:
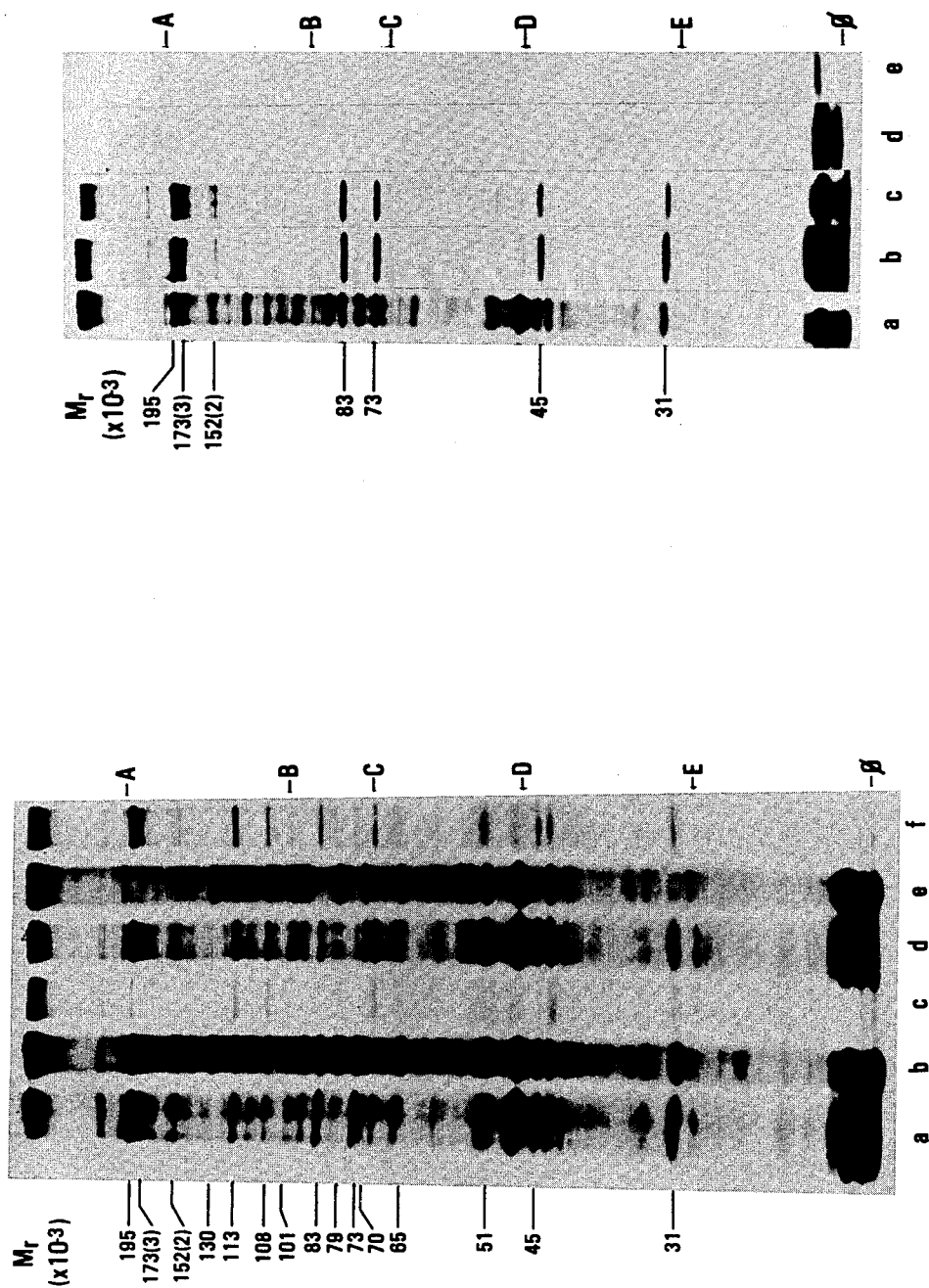
FIG. 2 depicts the fluorographic pattern obtained after SDS-PAGE of *Plasmodium falciparum* immune complexes from a pH 8 TX100-insoluble fraction of ICM. Figure designations are as in FIG. 1.

In FIG. 1, a representative gel comparing the molecular constituents of ICM and NM, treated first with pH 8 TX100 and then immediately with SDS sample buffer (to give a final 1% concentration SDS), is shown for ICM (FIG. 1, lane a) and NM (FIG. 1, lane d). This comparison was performed by loading material obtained from the same number of parasites into each lane (based on the number of parasites starting at the beginning of the culture period).

Although these preparations of ICM and NM were qualitatively similar, ICM contained larger quantities of p230, gp195, p173, p83, p73, p51, p45 and p31 antigens than did NM. The p173 antigen normally migrated as a triplet; although it is not readily visualized in the gel of FIG. 1, it was more easily seen in other gels. These data indicate that immune serum contained an activity (presumably antibody) that allowed a greater recovery of certain antigens from rupturing schizonts and agglutinated merozoites than was achieved from concurrent control cultures of NM.

Comparison of the pH 8 TX100 soluble and insoluble fractions of ICM and NM: Certain antigens, which were solubilized from NM by using pH 8 TX100 (FIG. 1, lane f), were less solubilized by a similar treatment of ICM (FIG. 1, lane c). Antigens of gp195, p173 (triplet), p152 (doublet), p113, p101, and p83, p73, p65, p51, p45 and p31 were present in the pH 8 TX100-soluble fraction of NM (FIG. 1, lane f), but were decreased (or not detectable) in the pH 8 TX100 soluble-fraction of ICM (FIG. 1, lane c).

The pH 8 TX100-insoluble fraction of ICM (FIG. 1, lane b) contained a number of antigens that were enriched relative the corresponding fraction of NM (FIG. 1, lane e) including p230, gp195, p173 (triplet), p152 (doublet), p113, p101, p83, p73, p51, p45 and p31. These results indicate that in ICM, antibody may have formed immune complexes with certain antigens rendering them insoluble in pH TX100. There were many additional pH 8 TX100-insoluble, labeled proteins in common between ICM and NM, making up a background of proteins not normally soluble in pH 8 TX100 (FIG. 1, lane e).

At least two parasite-derived proteins appeared as a result of extraction with pH 8 TX100. Proteins with $M_r$ 130 and 79 kDA appeared in the pH 8 TX100 insoluble fraction of both ICM and NM (FIG. 1, lanes b and e, respectively), but they were absent from ICM and NM that had been processed quickly by using SDS (FIG. 1, lanes a and d, respectively). These proteins appeared to be artifacts resulting from extracting parasites with Triton X-100.

Some pH 8 TX100-insoluble antigens from ICM are immune-complexed with antibody. The pH 8 TX100 pellet from ICM (FIG. 1, lane b) was washed and then treated with acidic TX100 at a pH low enough to dissociate antigen-antibody complexes. After separation of the insoluble and soluble fractions, the acidic TX100-soluble fraction was neutralized by adding Tris and was either prepared directly for SDS-PAGE, or was first treated with protein A (Pansorbin) to precipitate immune complexes. In the latter case, precipitation was achieved by antibodies complexed with antigens in the immune complexes.

As shown in FIG. 2, when the pH 8 TX100-insoluble fraction of ICM (lane a) was treated with acidic TX100, then p230, gp195, p173 (triplet), p152 (doublet), p83, p73, p45 and p31 antigens were solubilized (FIG. 2, lane b). All of these antigens were precipitated from the neutralized acidic extract by Pansorbin (FIG. 2, lane c) and were enriched for in comparison with other antigens from the pH 8 TX100-insoluble fraction of ICM (FIG. 2, lane a). Significantly, none of the antigens identified above were recovered when the neutralized acidic TX100 extract of a parallel NM control (FIG. 2, lane d) was treated with Pansorbin (FIG. 2, lane e). The number of antigens associated with the immune complexes thus appeared to be limited compared with the total number of antigens recognized by the immune serum, i.e., some pH 8 TX100-insoluble antigens from ICM are immune-complexed with antibody.

It was found that more antigens were recognized by FIS than were immune-complexed in ICM. Examination of long exposures of fluorographs of the pH 8 TX100-soluble fraction of [³H]-isoleucine-labeled NM and ICM revealed at least 66 bands from NM and at least 55 bands from ICM (data not shown). Immune serum precipitated at least 45 antigens from the pH 8 TX100-soluble fractions of schizont-infected erythrocytes and merozoites and at least 36 antigens from the pH 8 TX100-soluble fraction of NM. However, immune serum precipitated only 25 antigens from the corresponding fraction of ICM. Antigens not precipitated in large quantity from the pH 8 TX100-soluble fraction of ICM included p230, gp195, p173 (triplet), p152 (doublet), p113, p108, p83, p73, p51, p45 and p31, and were the same antigens that appeared to be present in the insoluble immune complexes in ICM.

Figures 3, 4:
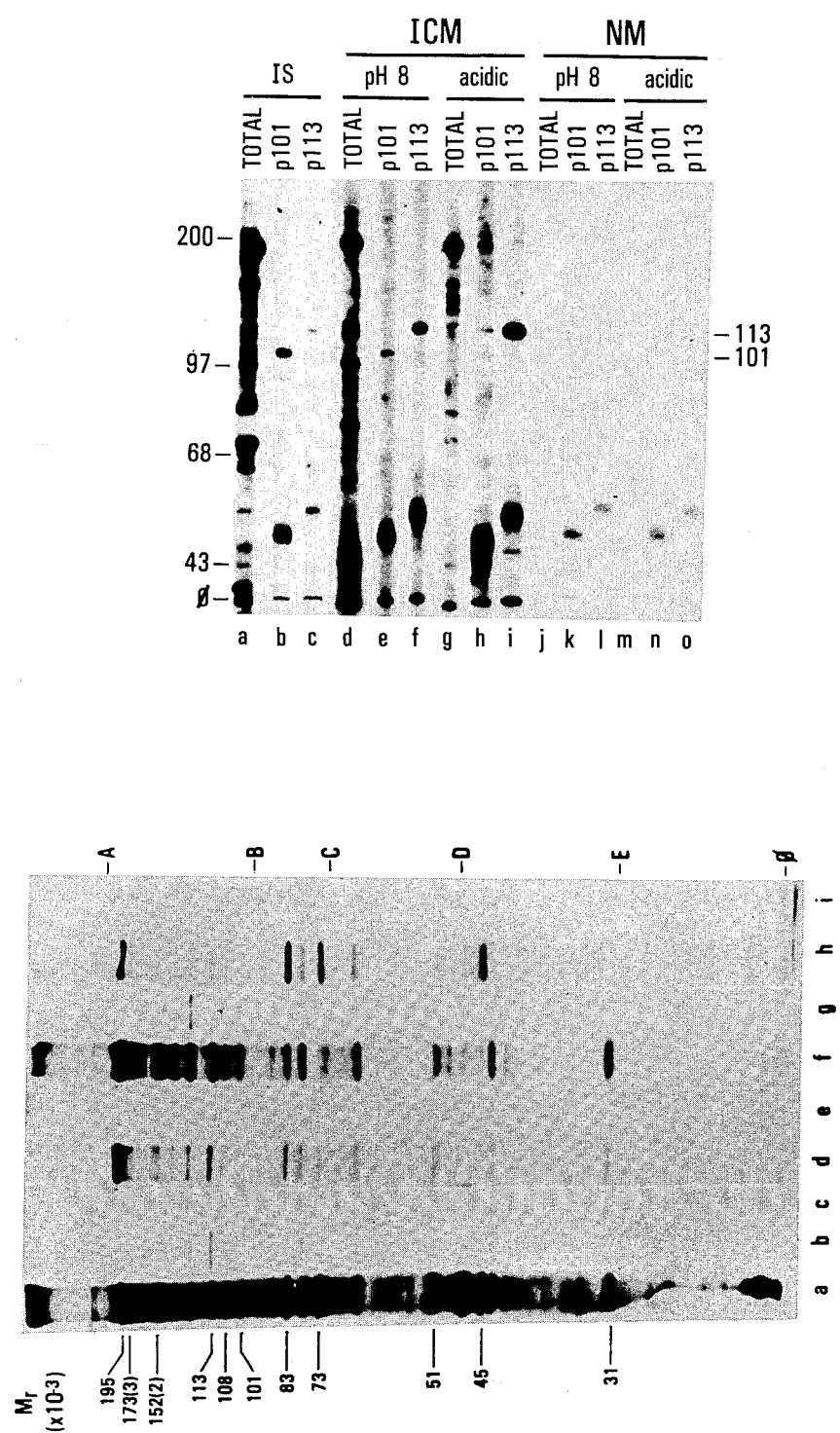
FIG. 3 shows the fluorographic pattern obtained after immunoprecipitation and SDS-PAGE of metabolically-labeled antigens from ICM, NM, schizont-infected erythrocytes, and spontaneously released merozoites of *Plasmodium falciparum*.
FIG. 4 shows the results of immunoblots prepared, using antibody dissociated from *P. falciparum* immune complexes, of total antigen and antigens affinity purified by means of monoclonal antibodies.

These data can be evaluated semiquantitatively by comparing FIG. 3, lane b (immunoprecipitation of the pH 8 TX100 soluble fraction of ICM) with FIG. 3, lane d (immunoprecipitation of the pH 8 TX100 soluble fraction of NM). Pansorbin treated with preimmune serum did not precipitate antigens from the pH 8 TX100-soluble fraction of ICM (FIG. 3, lane c), and precipitated only a small amount of p130 antigen from the corresponding fraction of NM (FIG. 3, lane e).

The results summarized above showed that antigens p230, gp195, p173 (triplet), p152 (doublet), p83, p73, p45 and p31 were complexed with antibody for the following reasons: (a) They were present in the pH 8 TX100-insoluble fraction prepared from ICM. (b) They became soluble when the pH of the pH 8 TX100 insoluble fraction was lowered to 2.8. (c) After neutralization, these acidic TX100-soluble immune complexes were precipitated by protein A (Pansorbin). Additional information about the specificity of the assay employed is found in the observation that fewer antigens were precipitated from the pH 8 TX100-soluble fraction of ICM than from NM, and those antigens that were missing from the pH 8 TX100-soluble fraction of ICM were present in the insoluble fraction. Antigens that were reduced or missing from the pH 8 TX100 soluble fraction of ICM had an $M_r$ of 230, 195, 173 (triplet), 152 (doublet), 113, 101, 83, 73, 51, 45 and 31 kDa, respectively.

The ICM thus possessed immune complexes containing antigens that were predominant both in merozoites (83, 73, and 45 kDa) and in schizont-infected erythrocytes (230, 195, 173 (triplet), 152 (doublet) 113, 101, 51, and 31 kDa) and these antigens represent only a restricted subset of the antigens synthesized by malaria parasites. The 83 and 45 kDa antigens correspond to merozoite surface antigens, which can be iodinated by using the lactoperoxidase method and are precipitated by monospecific antibodies against the 195 kDa precursor to these products. The p113 and p101 antigens are also associated with the surface of merozoites, and p230 is an antigen that is associated with the cytoplasmic face of infected erythrocytes. These immune complexes also contain a restricted set of antibody specificities against the identified antigens because, at membrane surfaces, immune complexes can form only between antibodies and the set of antigenic epitopes that are solvated and, hence, accessible to antibodies.

Thus, those antibodies which participate in the process of immune complex formation with accessible epitopes on membrane-bound or soluble surface antigens are defined as being functional, and they react with epitopes that are valuable immunogens.

EXAMPLE 2

Use of Immune-Complex Antibodies as Molecular Probes of Heterogeneous Polypeptide Mixtures One-dimensional immunoblotting of malaria antigens: P. falciparum (Camp) NM and ICM were prepared as described in Example 1. To dissociate the immune complexes, aliquots of NM and ICM were diluted to give a final concentration of $2.5 \times 10^8$ parasites per ml in pH 8 TX100. After incubating 20 min at room temperature, the supernates (pH 8 TX100 soluble) were separated from the pellets by centrifugation (3 minutes at $13,000 \times g$). After washing three times with pH 8 TX100, pellets (pH 8 TX100-insoluble) were resuspended in 0.2 M glycine HCl, pH 2.8, containing 1% TX100 (acidic TX100) and incubated 20 minutes at room temperature. After centrifugation ($13,000 \times g$; 3 minutes), the supernates (acidic TX100 soluble) were recovered. For immunoblotting reactions, as described below, acidic TX100 soluble extracts (or pH 8 TX100-soluble extracts mixed with an equal volume of acidic TX100) were neutralized by adding 12 μl (acidic TX100 soluble extract from $3 \times 10^6$ parasites) or 80 μl (pH 8 TX100-soluble extract from $1 \times 10^7$ parasites) to 4 ml Tris-buffered saline (10 mM Tris-HCl/150 mM NaCl, pH 8.2) containing 0.05% Tween 20 and 0.05% NaN$_3$ (TBS).

Crude-antigen preparations were affinity-purified for p101 and p113 using two monoclonal antibodies, prepared as described by Lyon et al, J. Immunol. 138: 895 (1986), that immunoprecipitated the two antigens, respectively. The crude and affinity-purified antigen fractions from 5 to $10 \times 10^6$ parasites were then each subjected to SDS-PAGE separation, in accordance with Example 1, as was a crude-antigen preparation. Antibody in total immune serum (IS), or antibody obtained from the dissociated immune complexes, was used to probe the resulting immunoblots (see FIG. 4). Antibodies reacting with p101 were more abundant in pH 8 TX100-soluble immune complexes (FIG. 4; compare lanes e and h). Antibodies reacting with p113 were more abundant in acidic TX100-soluble immune complexes (FIG. 4; compare lanes f and i).

The fact that, for both p101 and p113, antibodies reacting with affinity-purified antigens were present within immune complexes indicates that these antigens are involved directly in ICM immune complex formation. Consistent with this result is the reported observation that p113 induced partial protective immunity in a monkey model of P. falciparum malaria, further indicating that antigens present in ICM immune complexes are important targets of a protective immune response. By the same token, newly-discovered p101, like p113, is useful as an immunogen in malaria vaccines.

Two-dimensional immunoblotting of malaria antigens

ICM antigens from $5 \times 10^7$ parasites were extracted with 400 μl 1% SDS, to which was added 420 mg urea, 160 μl 20% TX100 and 750 μl of two-times concentrated ampholine buffers (LKB). The mixture was centrifuged at $30,000 \times G$ for 20 minutes to pellet nucleic acids. Aliquots of supernatant fluid containing antigens from $2 \times 10^6$ parasites were separated by nonequilibrium pH gradient electrophoresis for 5 hours, followed by SDS-PAGE with an 8% acrylamide separating gel. After electroblotting onto nitrocellulose, the resultant two-dimensional immunoblots were blocked with TBS containing 0.3% Tween 20. The immunoblots were probed with immune serum, probed with antibodies from acid soluble ICM immune complexes, probed with antibodies from pH 8 TX100-soluble ICM immune complexes, or probed with monoclonal antibodies of known specificity. Each immunoblot was then stained with colloidal gold (Janssen).

Figure 5A:
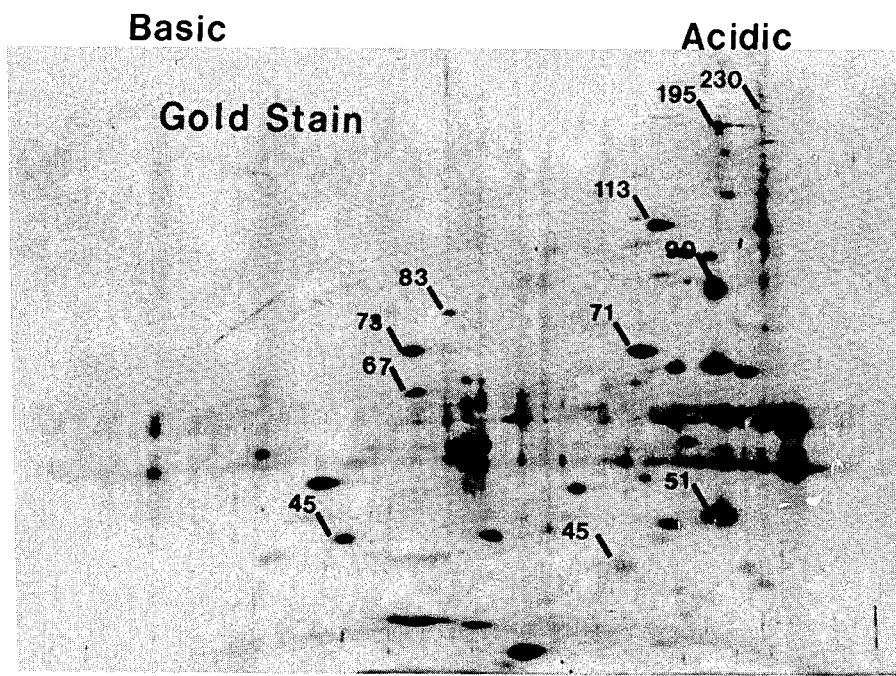
FIG. 5 shows two-dimensional immunoblots of *P. falciparum* antigens stained with colloidal gold (A), probed with functional immune serum (B), probed with antibodies from acidic TX100-soluble immune complexes (C), and probed with antibodies from pH 8 TX100-soluble immune complexes (D).
Figure 5B:
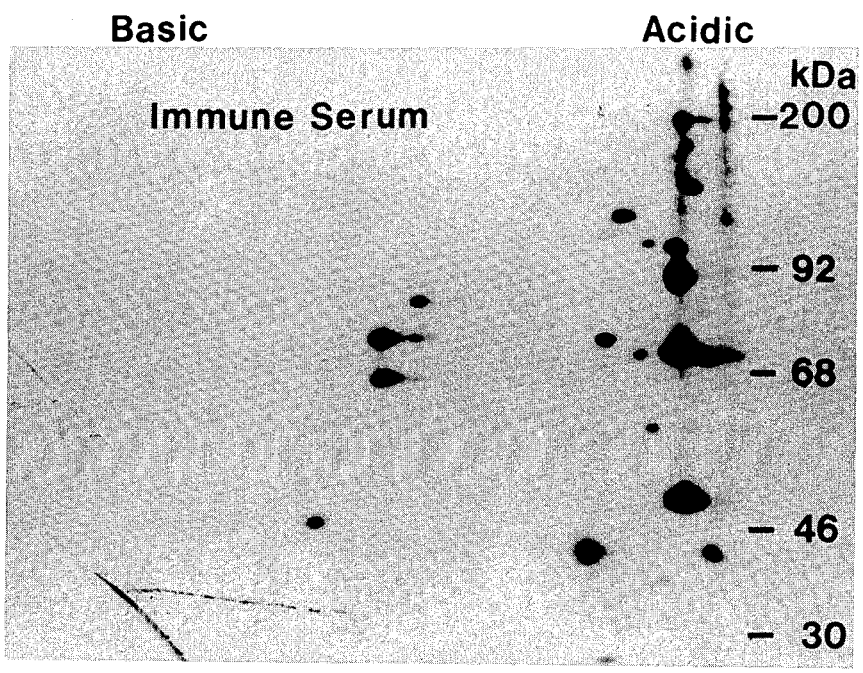
Figures 5C, 5D:
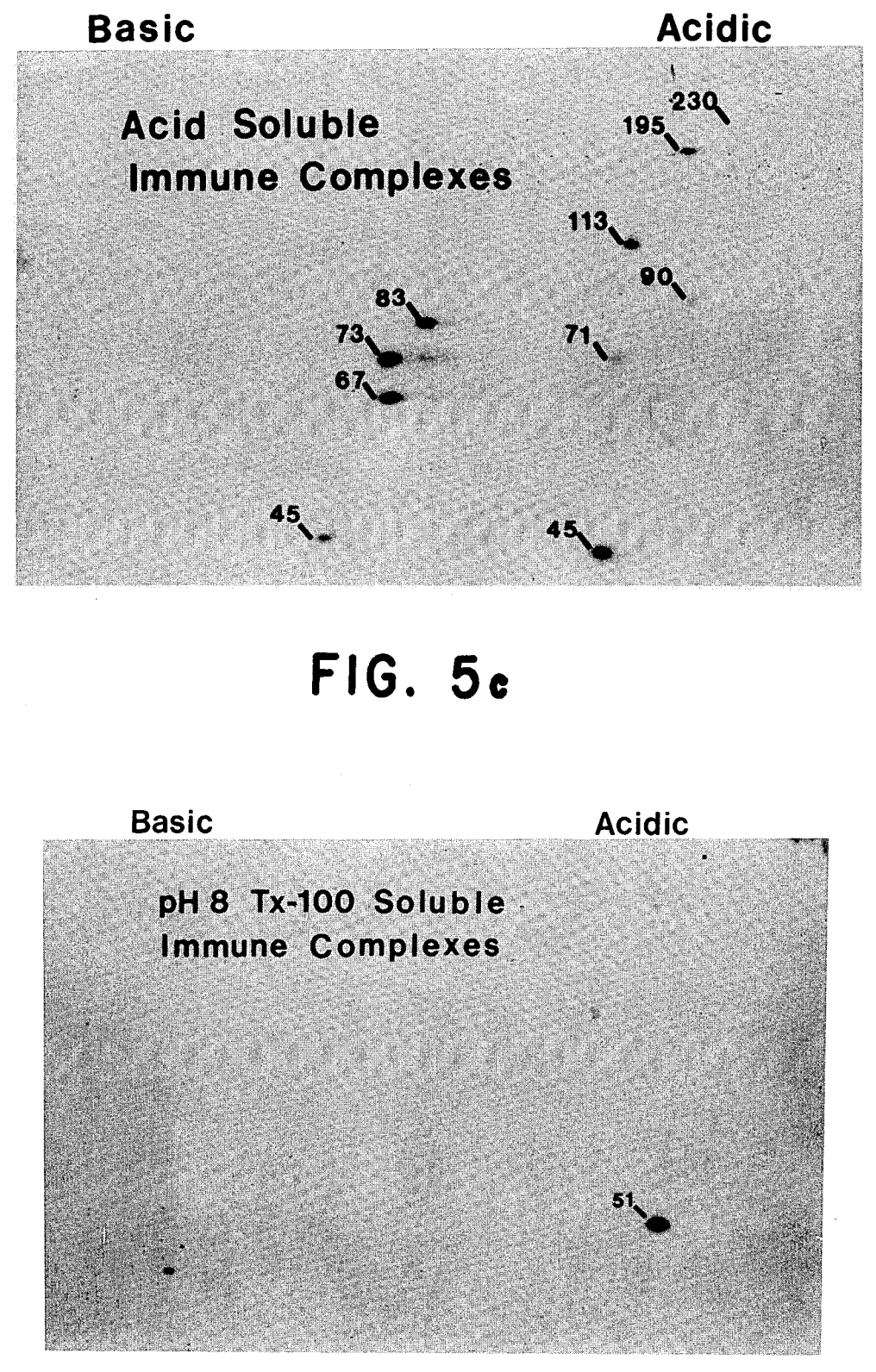

More than 100 proteins were stained with colloidal gold (FIG. 5A), and more than 80 of these were recognized by immune serum (FIG. 5B). In contrast, only 11 proteins (p230, gp195, p113, p90, p83, p73, p71, p67, p51, p45 and gp45) were recognized by antibodies from ICM immune complexes (FIG. 5C and 5D). Among these 11 proteins, six (gp195, p83, p73, p67, p45 and gp45) were recognized by monoclonal antibodies specific for the P. falciparum major merozoite surface glycoprotein (Lyon et al, 1987); two (p230 and p71) were recognized by a monoclonal antibody specific for a P. falciparum antigen localized at the cytoplasmic face of the infected erythrocyte membrane; and one (p113) was recognized by a monoclonal antibody used to affinity purify the p113 antigen that was present in ICM immune complexes (FIG. 4).

That a restricted set of P. falciparum antigens was recognized by antibodies present in immune complexes indicates that this subset of antigens is a target of the protective immune response observed in the animal from which FIS was obtained. These antibodies thus act in concert to form ICMs and, thereby, control infections in vivo. The fact that this subset includes antigens from more than one precursor protein explains why only partial protection has been achieved in vaccine trials carried out with gp195 or p113 individually.

Screening a P. falciparum expression library: On the order of $10^7$ P. falciparum (Camp) schizont-infected erythrocytes were cultured (5 hours at 37° C.) in 5% A076 FIS, prepared as described in Example 1. Antibodies contained in the resulting immune complexes were obtained, after extraction into pH 8 TX100, pursuant to the above-described protocol.

DNA from cultured P. falciparum merozoites was isolated following the method of Weber and Hockmeyer, Mol. Biochem. Parasitol. 15: 305 (1985), with an additional purification step of banding the DNA on CsCl gradients in the presence of ethidium bromide. The DNA was sheared by mung bean nuclease (Pharmacia P-L Biochemicals) digestion in either 35% or 40% formamide, using a range of 1 to 10 units of enzyme per μg of DNA, and the products of the different reactions were combined. The size of the resulting fragments ranged from 10 kb down to very small pieces, with DNA of about 1.5 kb giving maximum ethidium bromide staining. Ends of the DNA fragments were blunted with T4 DNA polymerase before addition of EcoR I linkers. Excess linkers were removed by EcoR I digestion and chromatography over Sephacryl S300, followed by a second round of digestion with EcoR I and chromatography.

The resulting DNA was ligated into the EcoR I site of the lac Z gene of λgt11 vector DNA treated with alkaline phosphatase as described by Young et al, *Proc. Natl. Acad. Sci. USA* 82: 2583 (1985). When grown in *E. coli* strain Y1090 according to Young and Davis, *Science* 222: 778 (1983), 90% of the phage in the library gave white plaques (and, therefore, contained inserted DNA) when plated in the presence of 5-bromo-4-chloro-3-indolyl-β-galactoside and isopropylthio-β-D-galactopyranoside (IPTG). On two plates, 80,000 phage plaques were produced by growth at 42° C. in *E. coli* Y1090. Lac Z gene expression was induced by an overlay of IPTG-treated nitro cellulose, which remained in contact with the plaques for 3 hours at 37° C., after which the filter was removed and blocked in TBS containing 0.3% BSA and 0.3% Tween 20 for 30 minutes at room temperature.

5 ml of antibody preparation derived from the immune complexes were applied to each filter and, after 1 hour to allow antibody binding, the filters were washed. To visualize antigen/antibody complexes, the filters were treated with a rabbit anti-Aotus IgG antibody/alkaline phosphatase conjugate and, thereafter, with the enzyme substrates nitro blue tetrazolium (NBT) and 5'-bromo-4'chloro-3'-indolylphosphate (BCIP). (To produce the conjugate, rabbits were immunized with protein A-affinity-purified Aotus IgG. Antibody against the Aotus IgG was purified on an Aotus IgG affinity column. After eluting the antibody from the column, alkaline phosphatase was conjugated to the antibody using glutaraldehyde.)

The binding of anti-Aotus IgG on the filters was evidenced by the formation of blue color. Of the 80,000 plaques adsorbed onto the filters, 20 were characterized by color formation indicative of antigen/antibody complexing. From these, five were selected at random for further study, and were clone purified.

The antigen-selected antibodies associated with the five clones were isolated, respectively, pursuant to the method described by Lyon et al, *Proc. Natl. Acad. Sci. USA* 83: 2989 (1986). Each antibody was then used to probe one-dimensional immunoblots of total-antigen preparations as described above. Immunoblots were rocked for 1 hour at room temperature in 5 ml of an antigen-selected antibody diluted 1:5 in TBS. The association of antibody with any of the antigen bands on the nitrocellulose blot matrix was visualized, as described above, using enzyme-labeled rabbit anti-Aotus IgG, NBT and BCIP.

Each of the five antibodies employed as probes reacted with a known merozoite surface glycoprotein, gp195, and its processed products. The respective identities of the reacting antigens was confirmed in parallel blots probed with monoclonal antibodies of well-characterized specificities as described by Lyon et al, *J. Immunol.* 138: 895 (1987). These results indicated that the clones identified by the immune-complex antibodies contained inserts of *P. falciparum* DNA encoding antigenic determinants of gp195.

DNA inserts from two of the clones were analyzed following restriction endonuclease digestion at the EcoR I site within the lac Z gene. The relative mobility of this insert DNA during electrophoresis in agarose gels was compared with commercially-available size markers (BRL). In this way, fragments of 1.5 and 3.4 kb were identified, and these were identical in size to clones from the same library (a50 and a119) that code for parts of gp195. See Lyon et al, *Proc. Natl. Acad. Sci. USA* 83: 2980 (1986).

EXAMPLE 3

Identification, Cloning and Sequencing of p101, an Antigen Belonging to the Subset of *P. falciparum* Antigens Participating in ICM Immune Complex Formation Monoclonal antibody (MAb) Pf12.3D5.3 (3D5) was produced from mice immunized with ICM immune complexes as described by Lyon et al (1987). MAb 3D5 recognized p101. Thus, in immunoprecipitation and immunoblotting reactions, MAb 3D5 recognized a *P. falciparum* antigen which migrated on SDS-PAGE in the same position as the 101 kDa antigen enriched in ICM preparations, and antibodies in the pH 8 TX100soluble fraction of ICM immune complexes recognized the 101 kDa antigen affinity-purified with MAb 3D5 (FIG. 4).

MAb 3D5 was coupled to Affigel-10 (Biorad) and used to affinity-purify p101. The purified p101 was bound to nitrocellulose filters and used to affinity-purify antibodies from FIS which were specific for p101.

A *P. falciparum* genomic DNA library was probed with FIS from monkey A076, and clones containing inserts recognized by the FIS were used to affinity purify antigen-specific antibodies from the FIS. Antigen-specific antibodies purifed using one such clone (a95) recognized p101 on immunoblots. *E. coli* Y1089 containing lysogenic phage a95 or control bacteriophage λ gt11 were cultured with (I) or without (U) IPTG, and total proteins were dissolved in SDS sample buffer and separated by SDS-PAGE. Expression products from clone a95 contained a fusion protein recognized by antibodies to β-galactosidase, by MAb 3D5, and by antibodies from FIS which were specific for p101 (FIG. 6). The DNA sequence of the insert in clone a95 was determined by standard methods and is shown in FIG. 7. Since clone a95 was identified with immune serum from a clinically immune animal, it is a vaccine candidate.

Identification of antigenic determinants recognized by antibodies from immune complexes (functional antibodies) can be accomplished by using any of several approaches. One method is to reclone fragments of the antigen gene that contain native sequences of DNA produced, for example, by restriction digestion, random shearing, or exonuclease digestion, into expression vectors. Those clones are then identified that express epitopes reacting with functional antibody. More than one restriction enzyme library can be prepared in order to optimize opportunities for identifying nonsequential epitopes and to locate epitopes more precisely.

Another method is to use functional antibodies to identify epitopes expressed in libraries constructed by randomly reassociating and ligating gene fragments produced by the methods identified above. In this way, detection of epitopes formed by the interaction of nonsequential parts of the gene product can be facilitated. The epitopes so identified can be defined with greater precision by creating peripheral and internal deletions and point mutations within the gene fragments that encode them. This would be accomplished by using methods such as limited exonuclease digestion, site-directed mutagenesis, and creation of internal deletions by ligating pieces of the insert obtained after directed restriction enzyme digestion, for example, with FokI primed with specific oligodeoxynucleotide sequences.

The foregoing examples illustrate the use, in accordance with the present invention, of molecular probes in the form of functional antibodies obtained from FIS via a kind of affinity purification in which an intact pathogenic unit is the substrate. By this approach, identification can be made of (1) antigens that are accessible, either individually or in combination, to functional antibodies in vivo: (2) multiple antigenic determinants on a single antigen that are accessible to functional antibodies; and (3) multiple antigens that are recognized by polyclonal functional antibodies, even when individual antigens of the group are themselves incapable of inducing protective antibodies.

The present invention also permits one to define the minimum-sized peptide, coded for by the genome of a pathogenic organism, that is required to form a particular functional epitope, i.e., an antigenic determinant recognized by a functional antibody. The present invention can be used, for example, to produce polypeptides that constitute naturally-occurring epitopes formed by interactions between nonsequential portions of a protein. This can be accomplished by identifying a DNA fragment as the shortest coding sequence for an epitope recognized by a functional antibody, or by identifying clones produced by random genetic deletions or rearrangements that still encode a peptide recognized by functional antibody.

In any event, the fragment determined by (recursive) application of immune-complex antibodies to expression products of ever more refined restriction-fragment libraries, following as described above, can be cloned and expressed to produce a peptide which can be used, either alone or in combination with an immunogenic carrier, in a vaccine against the pathogen of interest. A peptide of the present invention may thus be an immunogen, as in the case of $P. falciparum$ p101, p173 (triplet), p230, p51, p71 and p90; or it may be a hapten and, therefore, not immunogenic unless attached to a carrier.

The phrase "immunogenic carrier" is an art-recognized term denoting a molecule that is recognized by T helper ($T_h$) cells that enhance B cell responses to challenge by a hapten. Proteins are especially effective as immunogenic carriers, for example, because their great variety of potential carrier determinants per molecule can engage many $T_h$ cells. Like proteins, polysaccharides are exemplary of soluble molecules that can be used, as carriers, with haptenic peptides within the present invention. Particulate carriers such as liposomes and whole bacterial cells, or fragments of cells, are also suitable for this purpose. (Whole cells are generally killed, or their reproduction is hindered, in order to avoid problems associated with infection.)

With the present invention, any of a variety of immunogenic carriers can be used so long as the peptide-carrier complex is capable of inducing an immunogenic response to the hapten with which it is combined. When a soluble macromolecule, such as a protein, or a polysaccharide, is used as a carrier, molecular weights in the range of 10,000 to 1,000,000 are preferred. If sufficiently large, the protein or polysaccharide carrier may be insoluble and thus be considered to be a particulate material.

The method of associating a haptenic peptide of the present invention with an immunogenic carrier is also not critical, so long as the immunogenic specificity of the peptide is retained, at least in part. A preferred method of achieving this result is to attach a peptide to the carrier by means of an amide bond formed between a carboxylic acid or amino group of the carrier and an amino or carboxylic acid group of the peptide, particularly a free carboxylic acid or amino terminal group of the peptide. Another preferred method of bonding is the formation of an ester bond between a carboxylic acid or hydroxy group of the carrier and an hydroxy or carboxylic acid group of the peptide, preferably a terminal carboxylic acid group of the peptide. Linking groups, e.g., terminal diamines with 1 to 10 methylene carbons joining the amines, can be used if desired.

When a carrier is used with the present invention, the immunogenic response can be enhanced by bonding multiple peptides to the surface of the carrier. For example, from 1 to 100,000 peptides can be bound to a protein or polysaccharide with 100 to 10,000 being preferred. When proteins are used as a carrier, amphoteric proteins are preferred. Such proteins have a lipophilic portion and a hydrophilic portion. In such proteins, it is preferred to attach peptides of the invention to the hydrophilic region, thereby exposing them to the humoral environment when the lipophilic region becomes embedded in various membranes.

The present invention is particularly useful in the development of vaccines against pathogenic agents. With regard to malaria parasites, for example, nonhuman primates can be partially protected from malaria infections by immunization with certain antigens that have been purified from parasites, or with peptides derived from such antigens. The observed protection is insufficient to justify human vaccine trials with these antigens, however, and the reported results have indicated that a combination of antigens that would elicit antibodies that act synergistically may be needed to produce an effective vaccine. Yet selection of the appropriate antigens to combine has heretofore presented a considerable barrier to vaccine development.

Thus, a vaccine trial based on immunizing triplicate nonhuman primates or human volunteers with a single regimen of every possible combination of three antigens taken from a list of nine would require 1200 animals, excluding negative controls. Also, the prior-art approaches provided no indication as to which antigens should be combined to elicit a protective immune response.

In contrast, by analyzing immune complexes for their antigen content as well for their functional antibody content, pursuant to the present invention, antigens that can be used to advantage, either individually or in combination, to elicit protective immunity can be identified. Thus, identification of appropriate combinations of antigens by this approach can reduce significantly the numbers of animals or human volunteers required in an immunization trial. The present invention also allows the primary structure of protective B-cell epitopes to be deduced, and therefore permits the synthesis of peptide-based vaccines. It will be apparent to those skilled in the art that T-cell epitopes present on the antigens which are recognized by functional antibody, pursuant to the present invention, will be immunologically important, and that similar expression libraries can be used to identify these sites.

What is claimed is:

1. A method for selectively identifying surface-accessible antigens and surface accessible antigenic determinants of an intact pathogenic agent, comprising the steps of:
   (A) providing a sample comprising a plurality of intact units of a pathogenic agent,
   (B) contacting said sample with a heterogeneous mixture of antibodies from immune serum, such that antibodies from said mixture bind to antigenic determinant forming immune complexes on an intact unit of said plurality,
   (C) isolating said antibodies from said immune complexes,
   (D) obtaining defined fractions of a heterogeneous mixture of antigens produced by said pathogenic agent,
   (E) contacting said antibodies from step (C) with the separated heterogeneous mixture of antigens from step (D), and
   (F) identifying said separated antigens recognized by said antibodies.

2. A method according to claim 1, wherein step (D) comprises separating said heterogeneous mixture of antigens by gel electrophoresis to produce a banding pattern.

3. A method according to claim 1, wherein step (D) comprises (i) separating said hetergeneous mixture of antigens by gel electrophoresis to produce a banding pattern; and (ii) transferring said pattern onto a substrate.

4. A method according to claim 1, wherein step (D) comprises separating said heterogeneous mixture of antigens by pH-gradient electrophoresis followed by electrophoresis according to molecular weight, such that antigens are resolved in two dimensions.

5. A method according to claim 1, wherein step (D) comprises (i) separating said heterogeneous mixture of antigens by pH-gradient electrophoresis followed by electrophoresis according to molecular weight, such that antigens are resolved in two dimensions; and (ii) transferring said antigens onto a substrate.

6. A method according to claim 1, wherein said defined fractions of the heterogeneous mixture of antigens in step (D) comprise expression products from members of a library of genetic material from said pathogenic agent.

7. A method according to claim 1, wherein said defined fractions of the heterogeneous mixture of antigens in step (D) comprise expression products from members of a series of libraries of genetic material from said pathogenic agent, each library in the series yielding different expression products.

8. A method according to claim 1, wherein said defined fractions of the heterogeneous mixture of antigens in step (D) comprise expression products from members of a series of libraries of genetic material from said pathogenic agent, each library in the series yielding progressively smaller expression products.

* * * * *